United States Patent
Kogiso

(10) Patent No.: US 8,535,297 B2
(45) Date of Patent: Sep. 17, 2013

(54) TREATMENT INSTRUMENT FOR ENDOSCOPE

(75) Inventor: Junichi Kogiso, Tokyo (JP)

(73) Assignee: Olympus Medical Systems Corp., Tokyo (JP)

(*) Notice: Subject to any disclaimer, the term of this patent is extended or adjusted under 35 U.S.C. 154(b) by 1763 days.

(21) Appl. No.: 11/888,561

(22) Filed: Aug. 1, 2007

(65) Prior Publication Data

US 2008/0033239 A1      Feb. 7, 2008

(30) Foreign Application Priority Data

Aug. 3, 2006    (JP) ................. P2006-212076

(51) Int. Cl.
*A61B 17/00*    (2006.01)

(52) U.S. Cl.
USPC ............... 606/1; 600/139; 600/140; 600/141; 600/142; 600/143; 606/144

(58) Field of Classification Search
USPC ...................... 606/1; 600/139–144
See application file for complete search history.

(56) References Cited

U.S. PATENT DOCUMENTS

| 4,982,727 A | 1/1991 | Sato |
| 5,228,451 A | 7/1993 | Bales et al. |
| 2005/0124912 A1 | 6/2005 | Griego et al. |
| 2006/0111617 A1 | 5/2006 | Wimmer |
| 2007/0112359 A1 | 5/2007 | Kimura et al. |

FOREIGN PATENT DOCUMENTS

| EP | 1 820 457 A1 | 8/2007 |
| JP | H3-47246 | 2/1991 |
| JP | 8-280701 | 10/1996 |
| JP | 10-192231 | 7/1998 |
| WO | WO 2006/062019 A1 | 6/2006 |
| WO | WO 2006/062020 A1 | 6/2006 |

*Primary Examiner* — Aaron Roane
(74) *Attorney, Agent, or Firm* — Scully, Scott, Murphy & Presser, P.C.

(57) ABSTRACT

A clip device 1 that has a coil-shaped tubular body 6 that is inserted through a curvable treatment instrument insertion channel of an endoscope, the tubular body 6 includes a proximal side coil (first coil) 10 that has a spring constant per unit length of 15 N/mm to 500 N/mm and is disposed on the proximal end side of the tubular body 6; and a distal end side coil 11 that is connected to the distal end of the proximal side coil 10, has a greater inner diameter than the inner diameter of the proximal side coil 10, has a spring constant per unit length of 15 N/mm to 500 N/mm, and has a spring constant that differs from the spring constant of the proximal side coil 10, with the ratio of the spring constants of the proximal side coil 10 and the distal end side coil 11 is greater than 1.0 and less than or equal to 2.0. In accordance with the present invention, it is possible to provide a treatment instrument for an endoscope, in which even in a case where a strong compressive force is applied to the coil-shaped tubular body in a curved channel of endoscope, it is possible to suppress a plastic deformation of the tubular body due to a slippage of the coil wire.

11 Claims, 13 Drawing Sheets

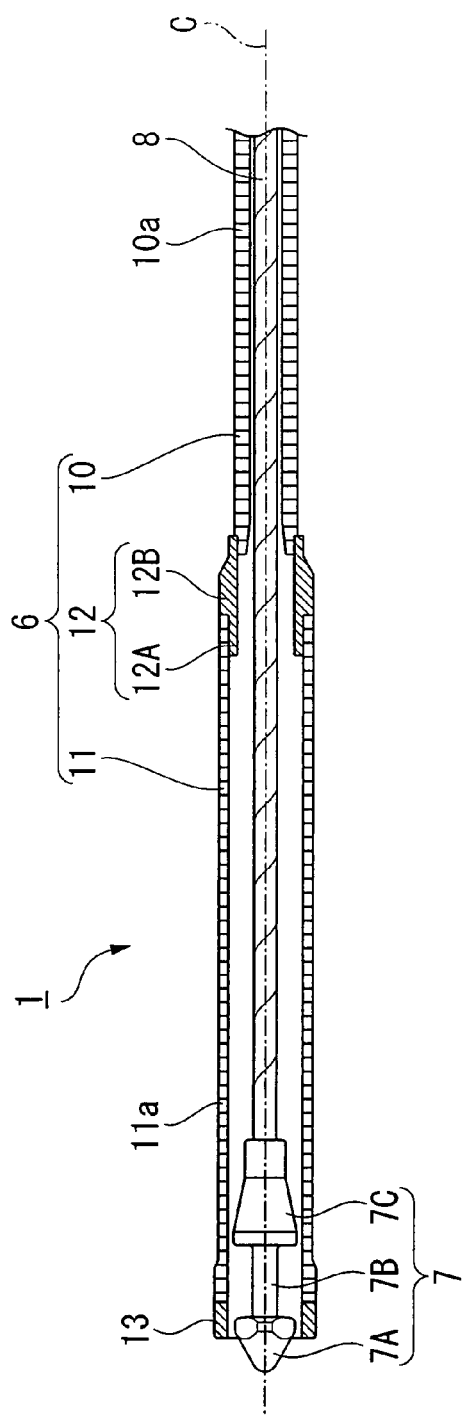
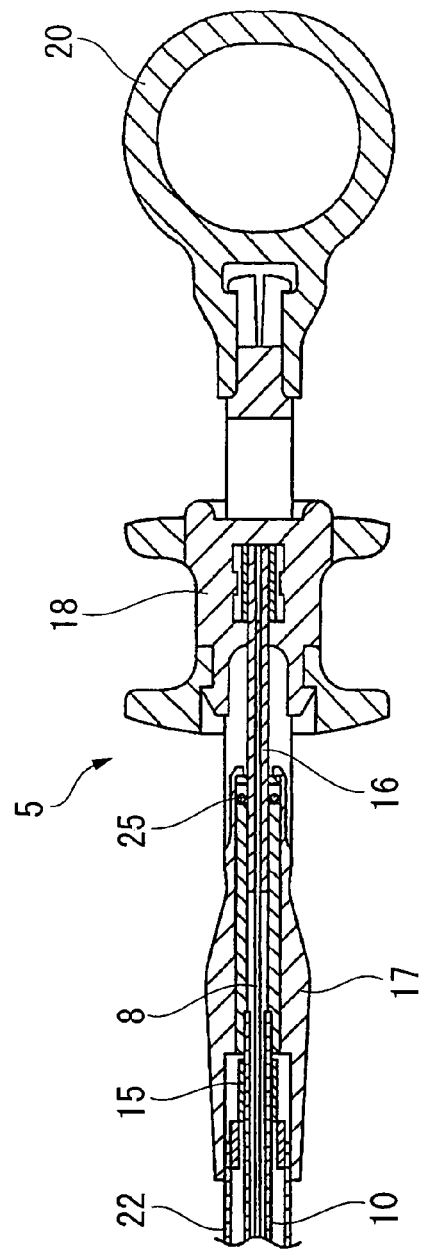
FIG. 2A
FIG. 2B

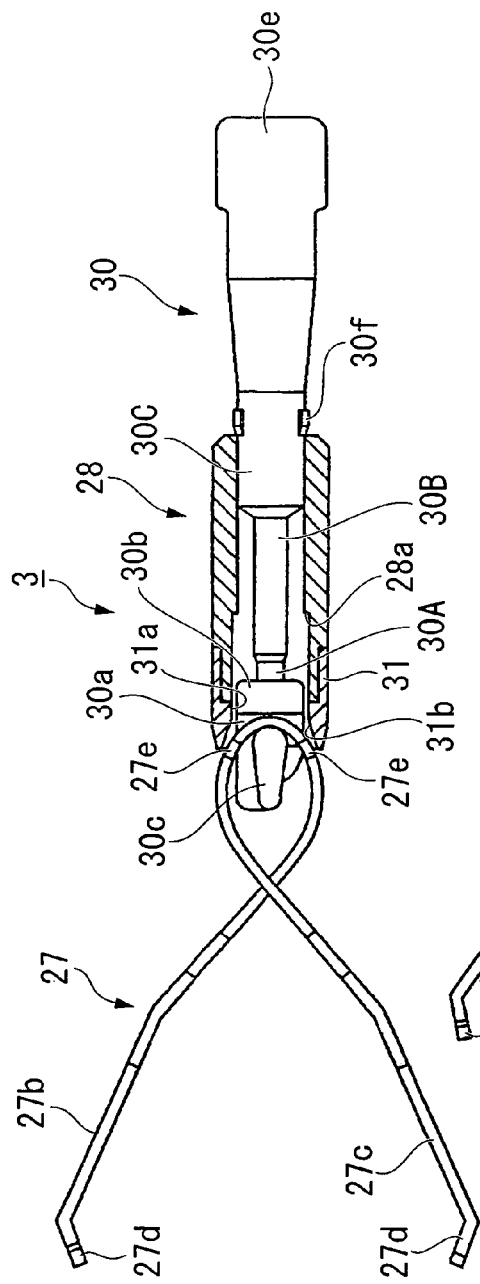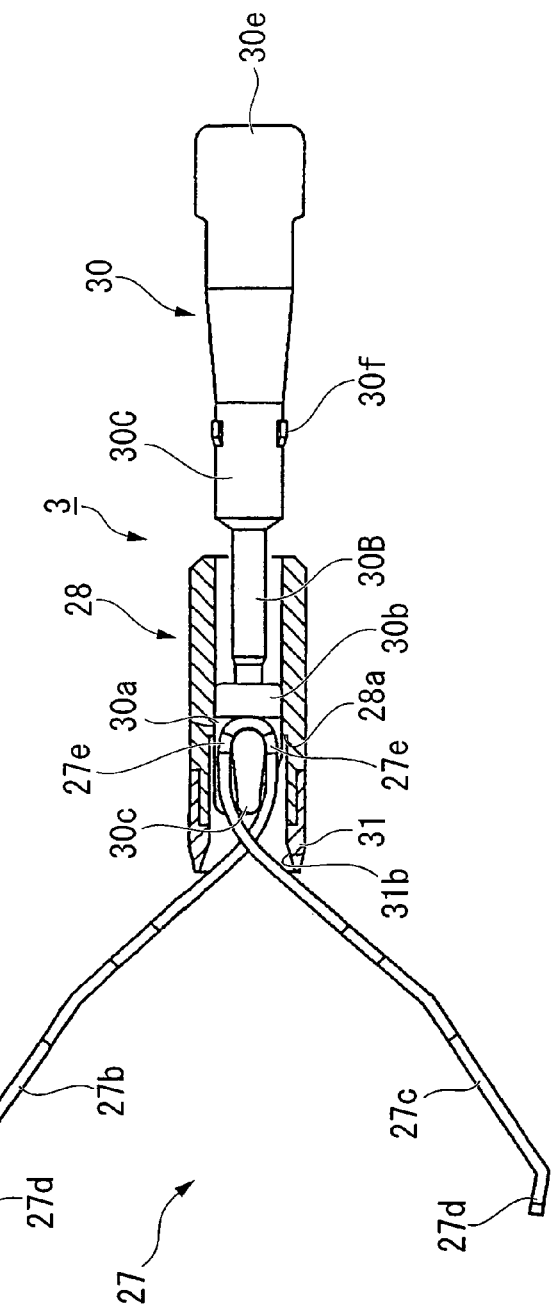

TREATMENT INSTRUMENT FOR ENDOSCOPE

BACKGROUND OF THE INVENTION

1. Field of the Invention

The present invention relates to a treatment instrument for an endoscope such as a clip device or biopsy forceps, and the like that is used with an endoscope having a soft insertion portion.

Priority is claimed on Japanese Patent Application No. 2006-212076, filed Aug. 3, 2006, the content of which is incorporated herein by reference.

2. Description of Related Art

Japanese Unexamined Patent Application No. H08-280701 discloses a clip device that is used with an endoscope having a soft insertion portion. In a treatment device such as the clip device, the insertion portion is formed of a tubular body that is formed of a coil of metal wire such as stainless steel, and an operation wire that is inserted in the tubular body and connected to a treatment tool that is disposed at distal end of the tubular body. A hook to which the treatment tool such as a clip unit is engaged is provided at the distal end of the operation wire via, for example, a cylindrical connecting member. The treatment tool, such as a clip unit, that is disposed or engaged at the distal end of the operation wire is activated by pulling an operating member such as the operation wire relative to the tubular body with a strong force.

To achieve a structure that facilitates operation by the operator even in the state of the tubular body being curved along the curvature of the insertion portion of the endoscope, the tubular body is constituted by a distal end side coil and a proximal end side coil being connected via a connecting portion that is harder than both. In this event, the distal end side coil is constituted to be softer than the proximal side coil. The tubular body is constituted by the proximal end portion of the distal end side coil and the distal end portion of the proximal side coil, which has a greater wall thickness and a smaller inner diameter than those of the distal end side coil, being directly connected by, for example, laser welding and the like.

As described above, in the connecting portion between the distal end side coil and the proximal end side coil, since the inner diameters mutually differ, a step arises due to the inner diameter differences at the connecting portion. For that reason, in the state of the two coils being curved into a curvature (for example, with a radius of 10 mm to 30 mm), for example, when a pulling force is impressed on the operation wire toward the proximal side during clipping of the clip unit or the like, a compressive force occurs on each coil.

SUMMARY OF THE INVENTION

A first aspect of the treatment instrument for an endoscope in accordance with the present invention is a treatment instrument for an endoscope that has a coil-shaped tubular body that is inserted through a curvable treatment instrument insertion channel of an endoscope, in which the tubular body includes a first coil that has a spring constant per unit length of 15 N/mm to 500 N/mm and a second coil that has a spring constant differing from the spring constant of the first coil and is coaxially connected with the first coil, in which the ratio of the spring constants per unit length of the first coil and the second coil is greater than 1.0 and less than or equal to 2.0.

A second aspect of the treatment instrument for an endoscope in accordance with the present invention is a treatment instrument for an endoscope that has a coil-shaped tubular body that is inserted through a curvable treatment instrument insertion channel of an endoscope, in which the tubular body includes a first coil that has a spring constant per unit length of 15 N/mm to 500 N/mm and a second coil that has a spring constant differing from the spring constant of the first coil and is coaxially connected with the first coil, in which a torsion spring constant per unit length of either the first coil or the second coil with a smaller spring constant per unit length is not less than 25 N mm/rad.

A third aspect of the treatment instrument for an endoscope in accordance with the present invention is a treatment instrument for an endoscope in which the first coil is disposed at the proximal end side of the tubular body, and the second coil is connected to the distal end of the first coil.

A fourth aspect of the treatment instrument for an endoscope in accordance with the present invention is a treatment instrument for an endoscope in which the inner diameter of the second coil is greater than the inner diameter of the first coil.

A fifth aspect of the treatment instrument for an endoscope in accordance with the present invention is a treatment instrument for an endoscope in which the first coil is disposed at the proximal end side of the tubular body, the second coil is connected to the distal end of the first coil, the inner diameter of the second coil is formed to be greater than the inner diameter of the first coil, and the spring constant per unit length of the first coil is greater than the spring constant per unit length of the second coil.

A sixth aspect of the treatment instrument for an endoscope in accordance with the present invention is an endoscope which is further provided with a connecting portion that has a greater hardness than the first coil and the second coil and that connects the first coil and the second coil.

BRIEF DESCRIPTION OF THE DRAWINGS

FIG. 2A is a sectional view showing a substantial part of the clip device in accordance with the first embodiment of the present invention.

FIG. 2B is a sectional view showing the operation portion of the clip device in accordance with the first embodiment of the present invention.

FIG. 6A is an explanatory drawing showing the state of use of the clip unit that is used together with the clip device in accordance with the first embodiment of the present invention.

FIG. 6B is an explanatory drawing showing the state of use of the clip unit that is used together with the clip device in accordance with the first embodiment of the present invention.

DETAILED DESCRIPTION OF THE INVENTION

A first embodiment in accordance with the present invention shall be described referring from FIG. 1 to FIG. 14.

Figure 1:
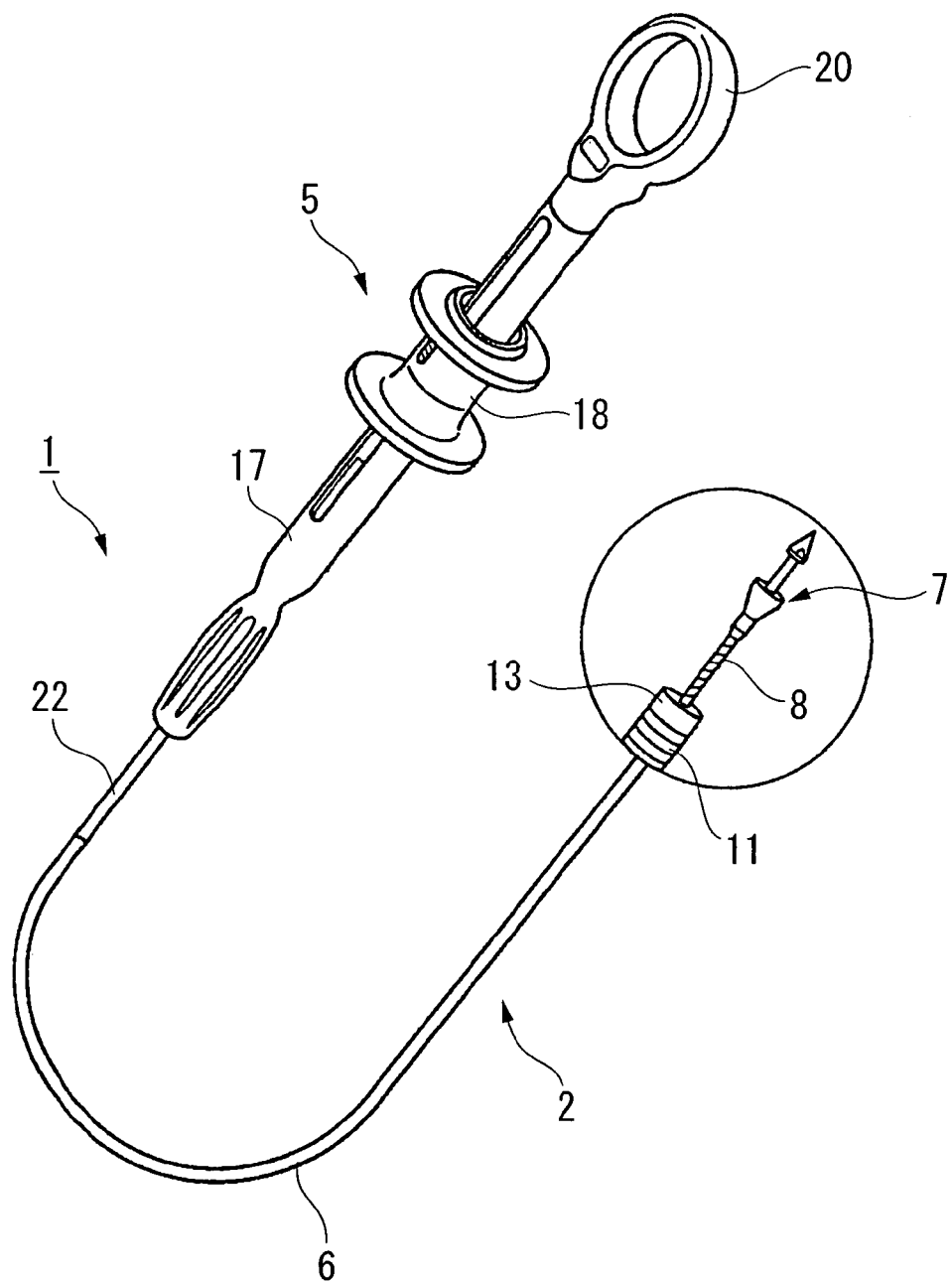
FIG. 1 is a block diagram showing the clip device in accordance with the first embodiment of the present invention.

A clip device (treatment instrument for an endoscope) 1 in accordance with the present embodiment is, as shown in FIG. 1, provided with an insertion portion 2 that is inserted into a body cavity and an operation portion 5 for performing opening/closing of a clip unit 3 described later that is mounted on the distal end of the insertion portion 2 and grabs biological tissue not shown.

The clip device 1 is inserted through a treatment instrument insertion channel of the endoscope insertion portion not shown for example, and used in combination with the endoscope. For this reason, the insertion portion 2 is formed sufficiently longer than the treatment instrument insertion channel. The insertion portion 2 is provided with flexibility so as to curve in conformance with the curvature of the endoscope insertion portion.

Figure 3:
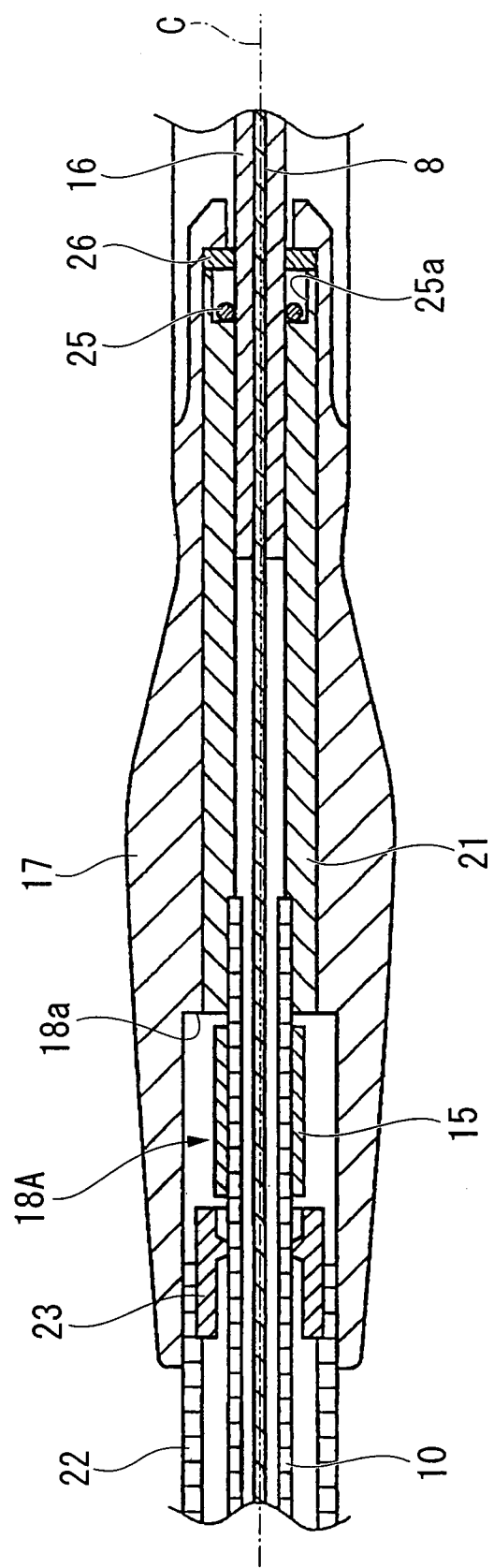
FIG. 3 is a sectional view showing a substantial part of the distal end portion of the operation portion of the clip device in accordance with the first embodiment of the present invention.

The insertion portion 2 is, as shown in FIG. 2 and FIG. 3, provided with a coil-shaped tubular body 6 that is inserted through the curvable treatment instrument insertion channel of the endoscope, and an operation wire 8 that extends along the tubular body 6 and is disposed to be inserted through the tubular body 6 so as to be freely extend and retract, with a hook (a large diameter portion) 7 having a larger diameter than the proximal end side of the operation wire 8 being connected to the distal end of the connecting wire 8 and the clip unit 3 being detachably engaged with the hook 7.

The tubular body 6 is provided with a proximal side coil (first coil) 10 having a spring constant per unit length of 15 N/mm to 500 N/mm disposed on the proximal end side of the tubular body 6; a distal end side coil (second coil) 11 that is connected to the distal end of the proximal side coil 10, has an inner diameter that is greater than the inner diameter of the proximal side coil 10, has a spring constant per unit length of 15 N/mm to 500 N/mm, and has a spring constant per unit length that differs from the spring constant per unit length of the proximal side coil 10; and a coil connecting pipe (connecting portion) 12 that has a greater hardness than the proximal side coil 10 and the distal end side coil 11, and connects the proximal side coil 10 and the distal end side coil 11.

The proximal side coil 10 is disposed at the proximal end portion of the coil connecting pipe 12. The proximal side coil 10 is formed of a flat wire 10a being tightly wound in a spiral, in which the flat wire 10a is made of a round wire of stainless steel with a substantially circular cross section rolled into a flat wire shape. The proximal side coil 10 is formed in a tubular shape as a whole with a substantially constant inner diameter. The proximal end portion of the coil connecting pipe 12 and the distal end portion of the proximal side coil 10 are fixed by welding or the like. The proximal side coil 10 is formed to have an inner diameter of approximately 1 mm and an outer diameter of approximately 2 mm to 2.4 mm. The outer surface side of the distal end portion of the proximal side coil 10 is ground to a predetermined depth.

The distal end side coil 11 is formed of a flat wire 11a being tightly wound in a spiral, in which the flat wire 11a is made of a stainless steel with a substantially rectangular cross section. The distal end side coil 11 is formed in a tubular shape as a whole with a substantially constant inner diameter that allows the clip unit 3 to insert through thereof. The distal end side coil 11 is formed to have an inner diameter of approximately 2 mm and an outer diameter of approximately 2.5 mm to 3 mm.

A distal end tip 13 that is formed of, for example, a stainless steel in a circular shape with an inner diameter of approximately 2 mm and an outer diameter of approximately 2 mm to 3 mm is disposed on the distal end of the distal end side coil 11. The distal end of the distal end tip 13 is smoothly rounded.

The coil connecting pipe 12 has a substantially pipe shape made of a stainless steel. It is formed of a distal end side connecting portion 12A and the proximal side connecting portion 12B connected together, in which the outer diameter of the distal end side connecting portion 12A is substantially the same as the inner diameter of the distal end side coil 11 and the inner diameter of the proximal side connecting portion 12B is substantially the same as the outer diameter of the proximal side coil 10. The inner diameters of the distal end side connecting portion 12A and the proximal side connecting portion 12B are substantially the same.

The inner surface side of the distal end portion of the distal end side connecting portion 12A and the inner surface side of the proximal side connecting portion 12B of the coil connecting pipe 12 are ground to predetermined depths respectively, and the proximal end portion of the distal end side coil 11 and the distal end portion of the proximal side coil 10 are fixed by, for example, welding or the like.

At the proximal end portion of the proximal side coil 10, as shown in FIG. 2B and FIG. 3, a coil receiving pipe 15 is disposed so as to cover a portion of the proximal end portion of the proximal side coil 10. The coil receiving pipe 15 is formed in a substantially pipe shape and is made of stainless steel. The inner diameter of the coil receiving pipe 15 is formed so as to follow the outer diameter of the proximal side coil 10, and is formed with an outer diameter of approximately 2 mm to 4 mm.

Here, letting the length of the side of the flat wire 11a vertical to the coil center axial line C of the distal end side coil 11 be a, the length of the side of the flat wire 11a parallel to the coil center axial line C of the distal end side coil 11 be b, the modulus of rigidity be G, the weight of unit volume be γ, the number of effective windings of the coil be n, and the coil average diameter be D, a spring constant per unit length k1 of the distal end side coil 11 is expressed as Equation (1). Hereinbelow, it is assumed that the line of action of an axial load and the center line of the coil agree, and a pitch angle is assumed to be small enough to ignore.

$$k1 = \frac{a^2 b^2 G}{\gamma n D^3} \quad (1)$$

Suppose the proximal side coil 10 is also wound with flat wire, a spring constant per unit length k2 is calculated with Equation (1).

In the case of the proximal side coil 10 being wound with round wire as it is, the spring constant per unit length k2 of the proximal side coil 10 is calculated with Equation (2), in which the wire diameter of the round wire is supposed to be d.

$$k2 = \frac{G d^4}{8 n D^3} \quad (2)$$

At this time, the spring constant per unit length k2 of the proximal side coil 10 is greater than the spring constant per unit length k1 of the distal end side coil 11, and the ratio of the spring constants per unit length of the proximal side coil 10 and the distal end side coil II is greater than 1.0 and less than or equal to 2.0.

Figure 4:
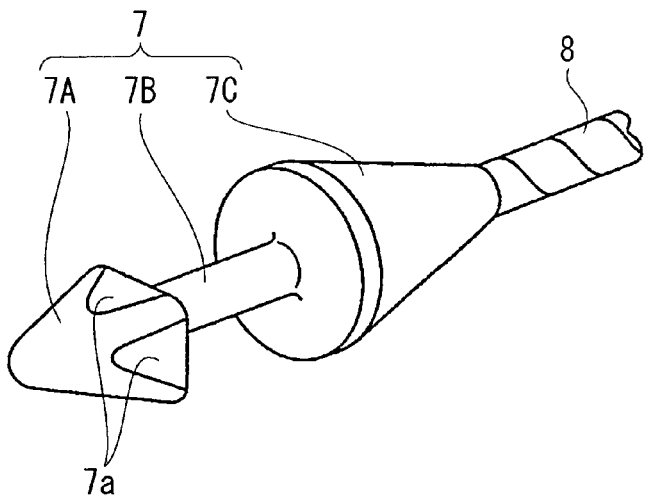
FIG. 4 is a perspective view showing a substantial part of the distal end portion of the operation wire of the clip device in accordance with the first embodiment of the present invention.

The hook 7 is used for hooking the clip unit 3. As shown in FIG. 4, the hook 7 is formed of metal material such as stainless steel, and is provided with a substantially conical shape engagement portion 7A that hooks and engages the clip unit 3, and a wire connecting portion 7C that connects the engagement portion 7A to the operation wire 8 by, for example, welding or the like, via a shaft portion 7B.

A plurality of flat surface portions 7a are formed on the side portions of the engagement portion 7A. For this reason, the engagement portion 7A has a shape of an arrowhead as a whole. The wire connecting portion 7C is formed in a substantially conical shape that contracts in diameter from the distal end portion side toward the proximal end portion side.

The operation wire 8 is formed by twisting solid wires made of metal such as stainless steel. As shown in FIG. 2B and FIG. 3, an operation pipe 16 is disposed at the proximal end portion of the operation wire 8. The operation pipe 16 is formed as a thin-walled pipe (wall thickness of approximately 0.1 mm) by a metal material such as stainless steel. The operation pipe 16 is caulked and fixed at the proximal end portion of the operation wire 8. The operation pipe 16 is longer than the motion stroke of a slider 18, which will be described below, and is disposed so as to cover the proximal end portion of the operation wire 8.

As shown in FIG. 2B, the operation portion 5 is provided with an operation portion body 17 to which the proximal end of the tubular body 6 is connected and the slider 18 to which the proximal end of the operation wire 8 is connected and that is disposed so as to freely extend and retract with respect to the operation portion body 17. A thumb ring 20 is mounted at the proximal end of the operation portion body 17 so as to be freely rotate with respect to the operation portion body 17.

On the central axial line C of the operation portion body 17, a hole 18A is formed having an inner diameter that is large on the distal end side, while at the proximal end side the inner diameter is smaller than the distal end side by interposing a step portion 18a therebetween. The proximal end of the hole 18A is blocked by the proximal end portion of the operation portion body 17, and a guide pipe 21 covers therein further on the proximal end side than the step portion 18a. At the distal end portion of the guide pipe 21, the proximal end portion of the proximal side coil 10 covers an interior portion thereof, and at the proximal end portion of the guide pipe 21, the operation pipe 16 covers the interior portion thereof.

At the distal end portion of the hole 18A, a cylindrical anti-break member 22 covers the interior portion thereof. The anti-break member 22 is connected to the outer circumferential surface of the proximal side coil 10 via an anti-break receiver 23. The anti-break receiver 23 is disposed further on the distal end side than the coil receiving pipe 15.

At the proximal end of the guide pipe 21, an O-ring housing portion 25a in which an O-ring 25 is housed is disposed. The O-ring 25 is arranged in the O-ring housing portion 25a, and has an inner diameter that is slightly smaller than the outer diameter of the operation pipe 16. For this reason, the inner circumferential surface of the O-ring 25 is in close contact with the outer circumferential surface of the operation pipe 16. A washer 26 is disposed at the proximal end portion of the guide pipe 21 so as to cover the O-ring housing portion 25a from the proximal end portion side.

Figure 5A:
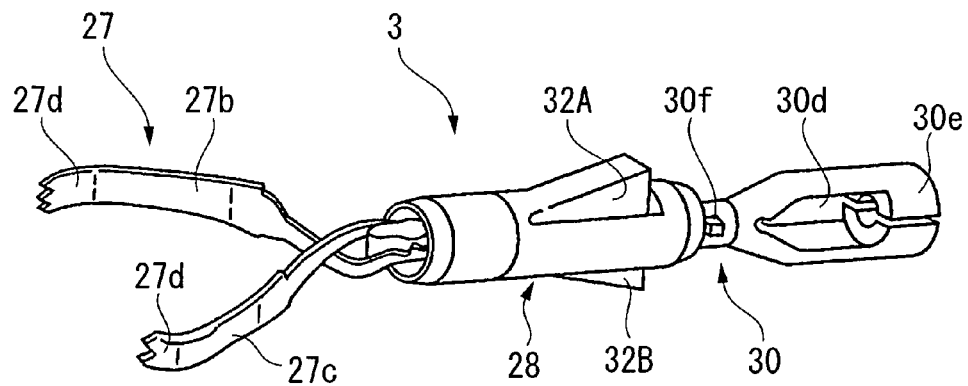
FIG. 5A is a perspective view showing the clip unit that is used together with the clip device in accordance with the first embodiment of the present invention.

The clip unit 3 used together with the clip device 1, as shown in FIG. 5A, includes a clip 27 that is made of a metal material plate such as a sheet spring material of stainless steel or the like; a pushing pipe 28 that moves with respect to the clip 27 to close the clip 27; and a coupling member 30 on which the hook 7 hooks.

Figure 5B:
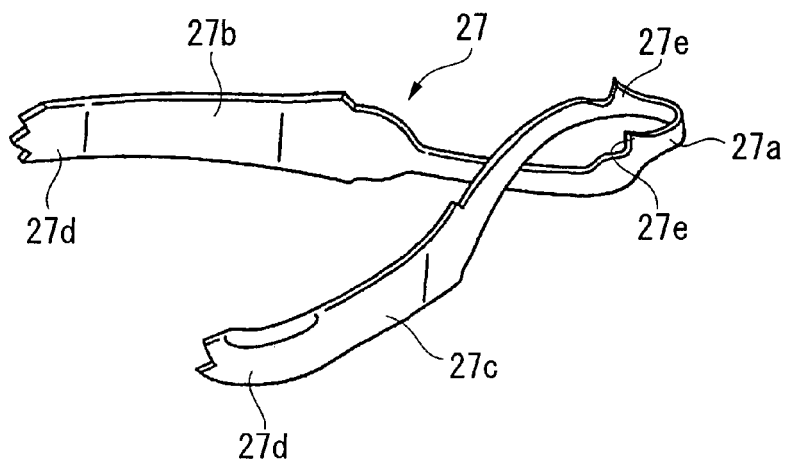
FIG. 5B is a perspective view showing the clip of the clip unit used together with the clip device in accordance with the first embodiment of the present invention.

As shown in FIG. 5B, a loop portion 27a is formed by folding back the clip 27 at its center portion, and a pair of arms 27b and 27c having an expansion tendency are extended so that the distal end sides thereof gradually separate after once intersecting with each other at a position in the vicinity of the loop portion 27a. Tissue grabbing parts 27d are formed at the distal ends of the pair of arms 27b and 27c.

The intersecting portions of the pair of arms 27b and 27c are formed to have a narrower width than the distal end sides thereof. The tissue grabbing parts 27d are provided so as to face each other. Saw-toothed shape protrusions 27e that protrude in the plate width direction are provided in the vicinity of the loop portion 27a of the pair of arms 27b and 27c. These protrusions 27e are formed to slide along the inner surface of the pushing pipe 28 with respect to the direction of pulling the clip 27 into the pushing pipe 28, but bite into the inner surface of the pushing pipe 28 with respect to the opposite direction.

The pushing pipe 28 is manufactured by injection molding a material that is softer than the clip 27, for example, a high-rigidity resin having a suitable degree of elasticity such as polyphthalamide (PPA) or polyamide (PA). The pushing pipe 28, by being fitted on the pair of arms 27b and 27c of the clip 27, closes the pair of arms 27b and 27c of the clip 27. An inner diameter step portion 28a is provided midway along the inner surface of the pushing pipe 28, so that the distal end side thereof is formed with a wider diameter than the proximal end side.

At the distal end portion of the pushing pipe 28, as shown in FIG. 6A and FIG. 6B, a distal end pipe 31 that is formed of a high-strength metal material such as stainless steel is fitted. The outer diameter of the distal end pipe 31 is the same as the outer diameter of the pushing pipe 28, and an inner diameter sloping portion 31b is formed on the inner surface of the distal end pipe 31 such that the inner diameter of the distal end pipe 31 slowly increases from a minimum inner diameter portion 31a of the proximal end portion to the distal end portion thereof. A pair of projection/retraction wings 32A and 32B (refer to FIG. 5A) that freely project and retract in an elastic manner in the radial direction are formed on the outer circumferential portion of the pushing pipe 28.

The coupling member 30 is manufactured by injection molding a high-strength resin material such as liquid crystal polymer or polyamide synthetic fiber. The coupling member 30 is formed in a substantially cylindrical rod shape, and a projecting portion 30a is formed at the distal end thereof. A base portion 30b of the projecting portion 30a is formed in a substantially disc shape. A flat, elliptical shaped protruding portion 30c elongated in the axial direction is formed at the distal end side of the projecting portion 30a. The loop portion 27a of the clip 27 is hooked on the protruding portion 30c, so that the clip 27 and the coupling member 30 are engaged.

The other end side of the coupling member 30 is branched into a two-forked shape. At the branch portion, an elastic arm portion 30e that is provided with a cutaway portion 30d (refer to FIG. 5A) to thereby hold the aforementioned hook 7 is formed. At the middle portion of the coupling member 30, from the distal end side toward the rear end side, a thin diameter portion 30A, an intermediate diameter portion 30B, and a large diameter portion 30C are formed. The dimensions of the thin diameter portion 30A are set so that it breaks when a breaking force with the amount of, for example, 20 N to 60 N is applied. Moreover, the outer diameter of the large diameter portion 30C is set so that it closely covers the inner circumferential surface of the pushing pipe 28, and locking projections 30f are provided in a portion of the outer circumferential surface thereof.

Next, the action of the clip unit 1 in accordance with the present embodiment shall be described.

First, the slider 18 of the operation portion 5 is moved until abutting the proximal end side near the thumb ring 20. At this time, the distal end of the hook 7 shown in FIG. 2A is disposed inside of the distal end side coil 11.

Then, the slider 18 is moved to the distal end side direction away from the thumb ring 20. At this time, the hook 7 projects relative to the distal end tip 13 of the distal end side coil 11 by the operation wire 8. Then, the distal end portion of the hook 7 is abutted with the elastic arm portion 30e of the coupling member 30, and the slider 18 is moved further to the distal end side. At this time, the elastic arm portion 30e is spread apart outward by the engagement portion 7A of the hook 7. Then, when the hook 7 is pushed further into the elastic arm portion 30e, the elastic arm portion 30e closes with its resilient force after the hook 7 passing over thereof, so that the shaft portion 7B is grabbed by the elastic arm portion 30e. For this reason, the engagement portion 7A of the hook 7 engages with the elastic arm portion 30e. Thus, the clip unit 3 is coupled to the operation wire 8.

Next, by moving the slider 18 to the proximal end side, the clip unit 3 is pulled into the distal end side coil 11 via the operation wire 8. At this time, the projection/retraction wings 32A and 32B of the pushing pipe 28 are pushed to the inside to be pulled into the pushing pipe 28. For this reason, the clip unit 3 is drawn into the distal end side coil 11 without the projection/retraction wings 32A and 32B being caught on the end surface of the distal end tip 13.

At this time, the pair of arms 27b and 27c of the clip 27 are closed in conformance with the inner diameter of the distal end side coil 11. Here, since the projection/retraction wings 32A and 32B of the pushing pipe 28 are in contact with the inner surface of the distal end side coil 11, the state in which they were housed inside the pushing pipe 28 by undergoing elastic deformation is maintained, whereby the clip unit 3 is drawn into the distal end side coil 11.

Figure 7:
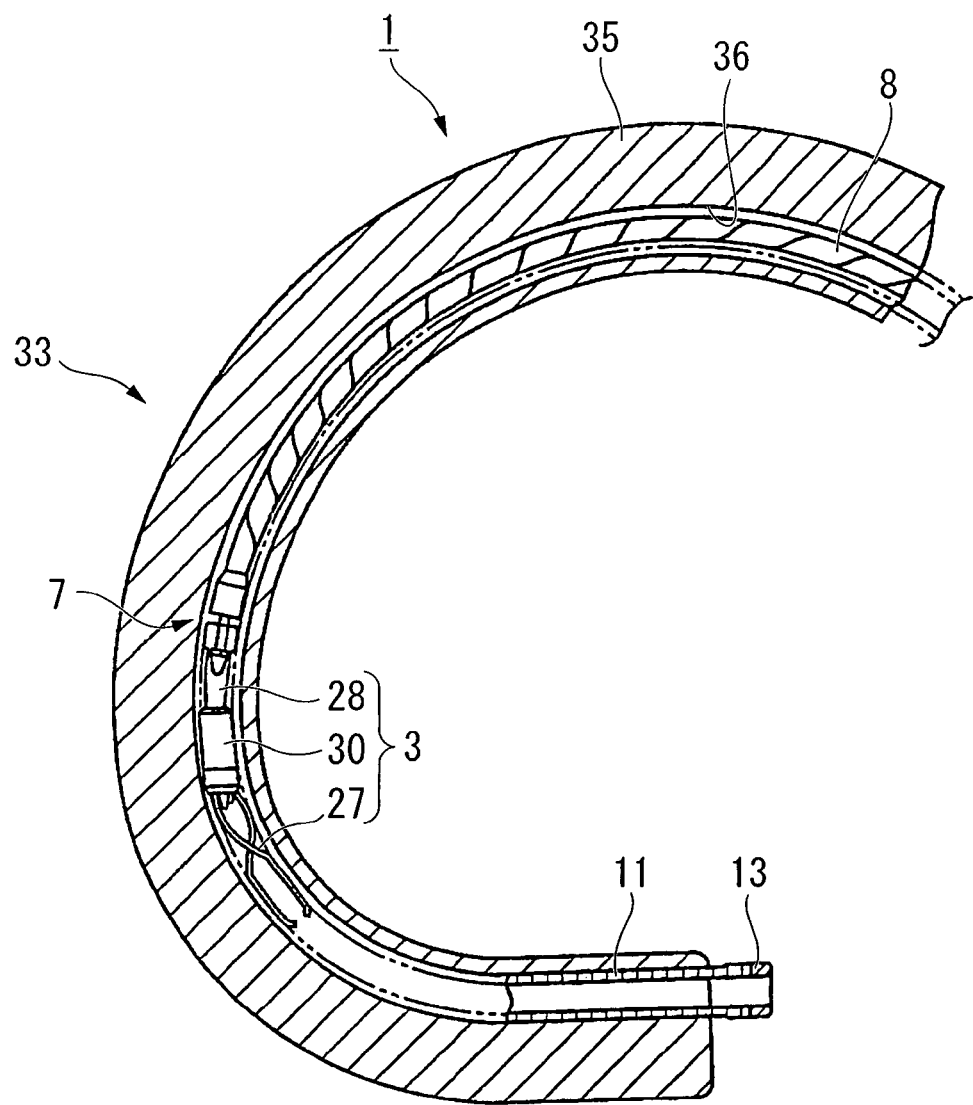
FIG. 7 is a sectional view showing a substantial part in a state that the clip device in accordance with the first embodiment of the present invention is used by inserting through the endoscope insertion portion.

Next, as shown in FIG. 7, the insertion portion 2 is guided into a body cavity through a treatment instrument insertion channel 36 of an endoscope insertion portion 35 of the endoscope 33 that has been inserted into the body cavity in advance. While observing the body cavity with the endoscope 33, the distal end of the insertion portion 2 is guided to the vicinity of the object portion. At this time, for example, as shown in FIG. 7, in the state of the radius of curvature of the curving portion of the endoscope insertion portion 35 being 15 mm or more, the distal end side of the tubular body 6 is projected from the treatment instrument insertion channel 36.

Figure 8A:
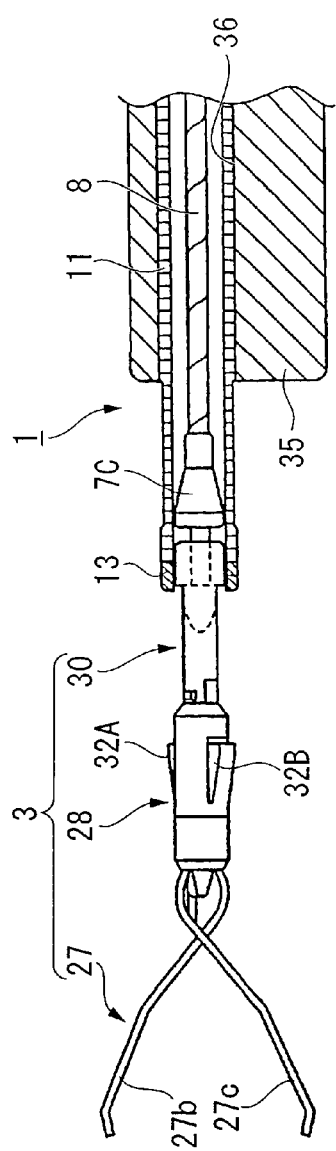
FIG. 8A is an explanatory diagram showing a state in which the clip of the clip unit is opened by using the clip device in accordance with the first embodiment of the present invention

By pushing the slider 18 to the distal end side with respect to the operation portion body 17, the clip unit 3 is advanced with respect to the tubular body 6 via the operation wire 8. At this time, the projection/retraction wings 32A and 32B of the pushing pipe 28 have inclined surfaces with a slope downward toward the distal end side, whereby the clip unit 3 is pushed out smoothly and without resistance from the distal end side coil 11. The projection/retraction wings 32A and 32B of the pushing pipe 28 are then released from the state of being in contact with the inner surface of the tubular body 6 and project outward in the radial direction of the pressing pipe 28. Meanwhile, since the pair of arms 27b and 27c of the clip 27 are provided with an expansion tendency, as shown in FIG. 8A, they open to some extent at the same time they project from the distal end side coil 11.

Figure 8B:
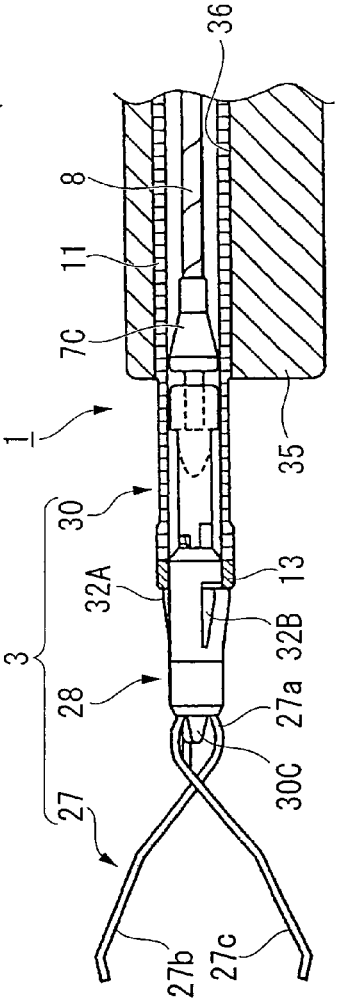
FIG. 8B is an explanatory diagram showing a state in which the clip of the clip unit is opened by using the clip device in accordance with the first embodiment of the present invention

After that, when the slider 18 is retracted to the proximal end side, as shown in FIG. 8B, the operation wire 8 is pulled back to the proximal end side and the proximal end side end surfaces of the projected projection/retraction wings 32A and 32B engage with the end surface of the distal end tip 13.

Figure 8C:
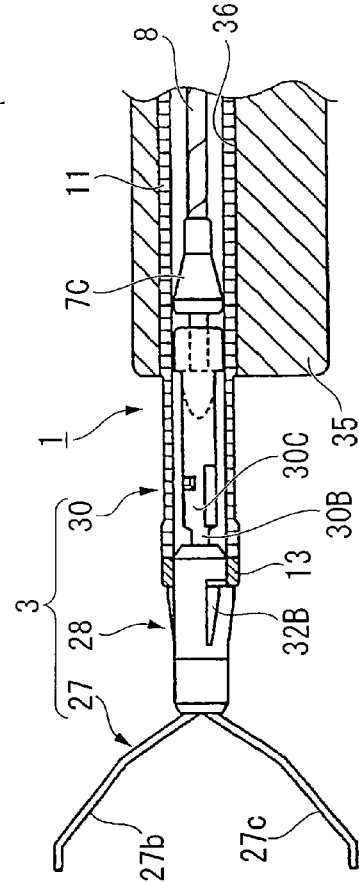
FIG. 8C is an explanatory diagram showing a state in which the clip of the clip unit is opened by using the clip device in accordance with the first embodiment of the present invention.

By further moving the slider 18 to the proximal end side to pull back the operation wire 8, as shown in FIG. 8C, the loop portion 27a of the clip 27 is pulled into the pushing pipe 28 via the coupling member 30, whereby the clip 27 opens. Then, the protrusions 27e of the clip 27 come into contact with the inner diameter step portion 28a of the pushing pipe 28 and the pair of arms 27b and 27c open to the maximum.

In this state, while observing an object portion of biological tissue not shown with the endoscope, the clip 27 is made to approach the object portion, and the tissue grabbing parts 27d of the clip 27 press the object portion. At this time, while relatively rotating the slider 18 with respect to the thumb ring 20 of the operation portion 5, the orientation of the clip 27 is adjusted.

Figure 9A:
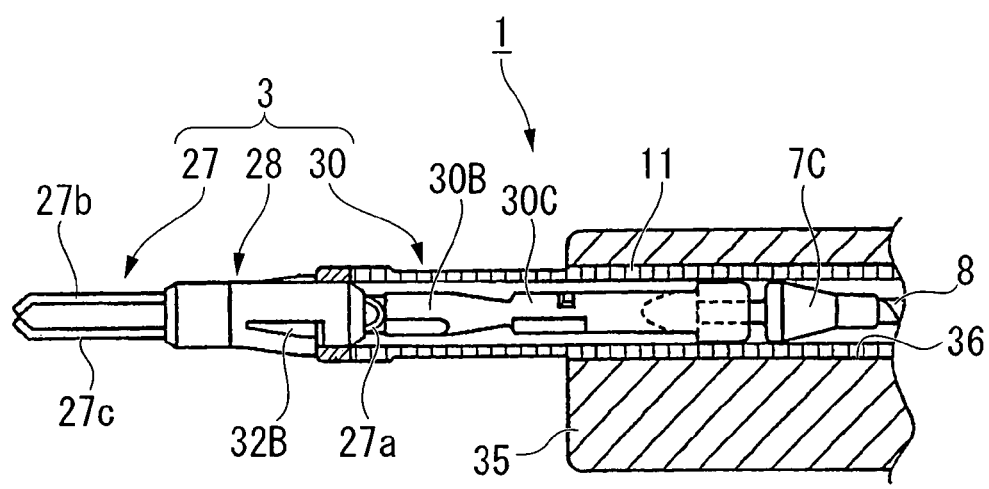
FIG. 9A is an explanatory diagram showing a state in which the clip of the clip unit is closed by using the clip device in accordance with the first embodiment of the present invention.

When the slider 18 is moved further to the proximal end side, the operation wire 8 retracts, and the pair of arms 27b and 27c of the clip 27 are pulled into the pushing pipe 28 via the coupling member 30. At this time, the protrusions 27e of the clip 27 pass over the inner diameter step portion 28a of the pushing pipe 28, and as shown in FIG. 9A, the pair of arms 27b and 27c of the clip 27 close, leading to a state in which the biological tissue is reliably clipped between the pair of arms 27b and 27c of the clip 27.

At this time, since the pushing pipe 28 is formed of a resin material that has a suitable degree of elasticity softer than the clip 27, the protrusions 27e of the clip 27 bite into the inner wall of the pushing pipe 28. Thereby, movement of the clip 27 in the axial direction inside of the pushing pipe 28 is constrained, so that the clip 27 is maintained in a closed state. On the other hand, the pair of projection/retraction wings 32A and 32B of the clip unit 3 push the distal end tip 13, whereby a strong compressive force is loaded on the tubular body 6 in the axial direction.

Figure 9B:
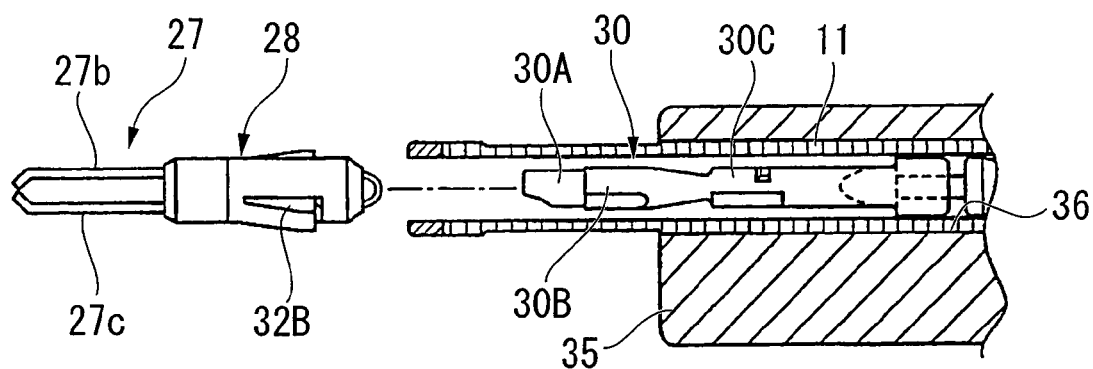
FIG. 9B is an explanatory diagram showing a state in which the clip of the clip unit is indwelled by using the clip device in accordance with the first embodiment of the present invention.

By moving the slider 18 further to the proximal end side to retract the operation wire 8, the thin diameter portion 30A of the coupling member 30 of the clip 27 breaks in the state of the strong compressive force being loaded on the tubular body 6 in the axial direction, as shown in FIG. 9B. Therefore, the coupling of the clip 27 and the coupling member 30 is released. Accordingly, the clip unit 3 breaks away from the clip device 1 to be indwelled in the body cavity with the biological tissue still gripped. Meanwhile, the tubular body 6 is released from the compressive force.

After the clip 27 is indwelled, the insertion portion 2 of the clip device 1 is removed from inside of the treatment instrument insertion channel 36 of an endoscope insertion portion 35. When reloading the clip unit 3, the remaining coupling member 30 is removed from the hook 7 and a new clip unit 3 is mounted.

Figure 10:
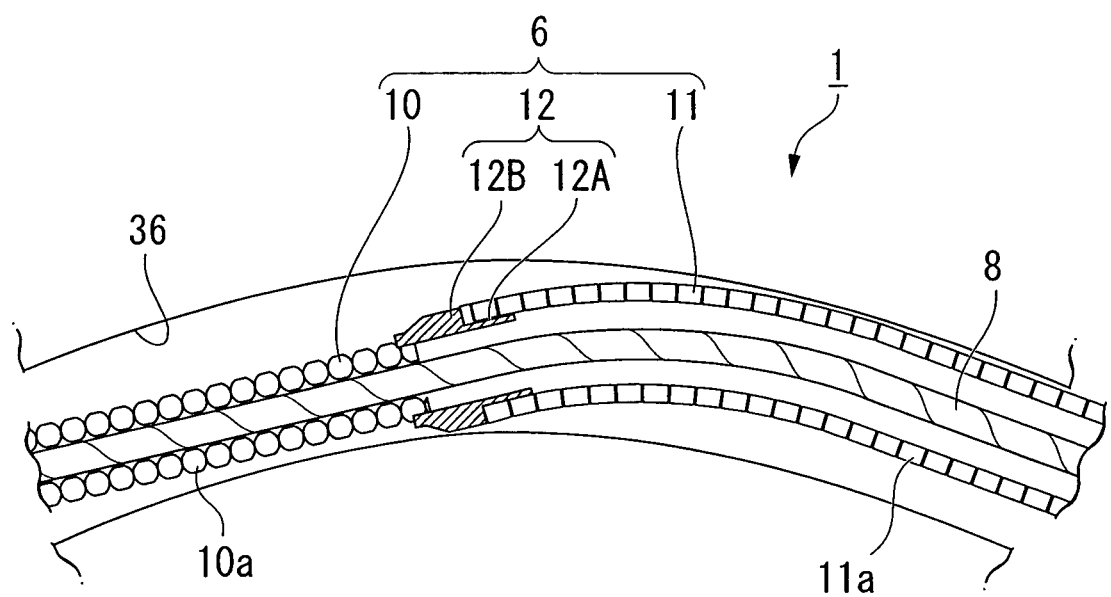
FIG. 10 is an explanatory diagram showing an action of the clip device in accordance with the first embodiment of the present invention.

Here, a compressive force is loaded to the insertion portion 2 of the clip device 1 which is in the state of curving along with the curvature of the treatment instrument insertion channel 36 as shown in FIG. 10 until the thin diameter portion 30A of the coupling member 30 breaks following the closure of the pair of arms 27b and 27c of the clip 27. For this reason, in the vicinity of the distal end side connecting portion 12A of the coil connecting pipe 12 in which the hardness discontinuously changes, a bending stress occurs on the distal end side coil 11 which has a smaller spring constant per unit length.

However, in accordance with the clip device 1, the ratio of the spring constants per unit length of the distal end side coil 11 and the proximal side coil 10 is greater than 1.0 and less than or equal to 2.0. Therefore, even if a compressive force is loaded in the axial direction in the state of the tubular body 6 being curved, it is possible to suppress concentration of bending stress at the proximal end portion of the distal end side coil 11 which has the smaller spring constant per unit length. Accordingly, even when a strong compressive force is applied to the tubular body 6 in the treatment instrument insertion channel 36 of the endoscope 33 that is curved, it is possible to suppress plastic deformation of the tubular body 6 due to slippage in the winding state of the flat wire 11a of the distal end side coil 11.

Also, since the distal end side coil 11 is softer than the proximal side coil 10, when inserted in the treatment instrument insertion channel 36 which is curved, it readily curves along the treatment instrument insertion channel 36, thereby improving operability related to the indwelling of the clip 27.

Figure 11:
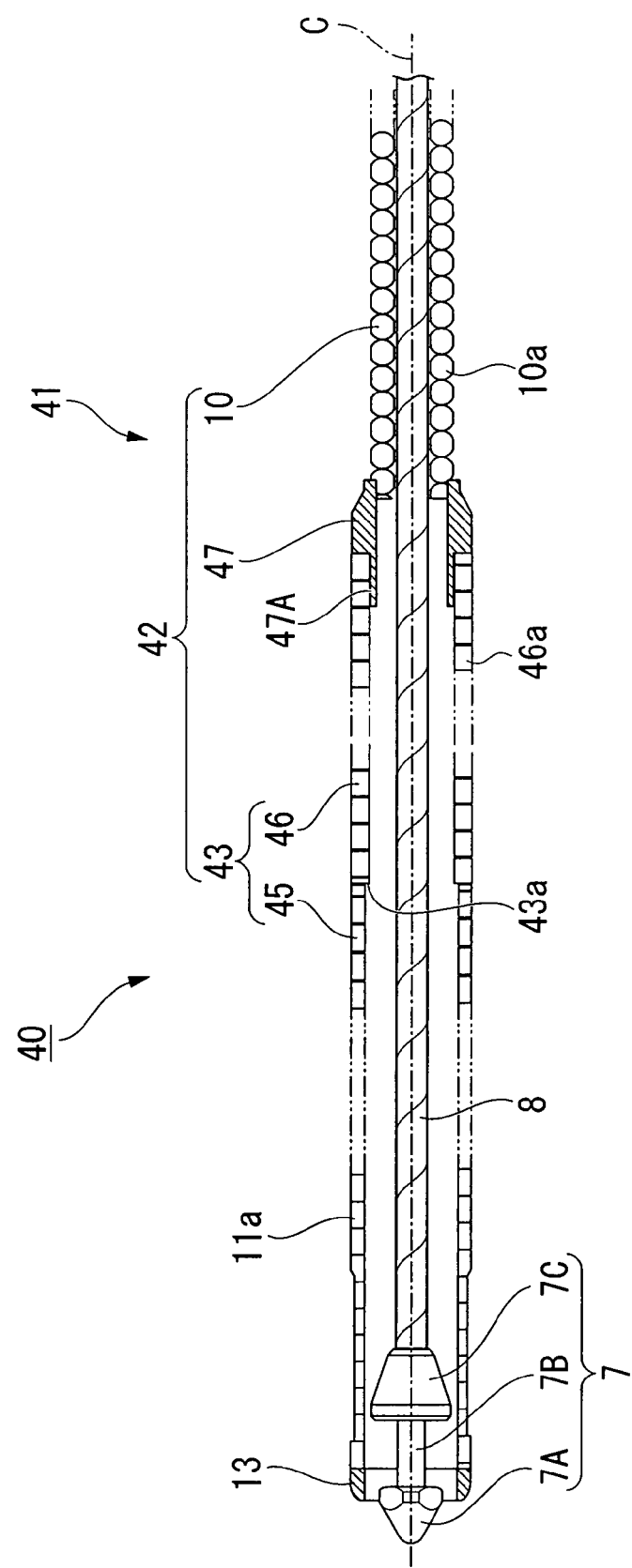
FIG. 11 is a sectional view showing a substantial part of the clip device in accordance with the second embodiment of the present invention.
Figure 12:
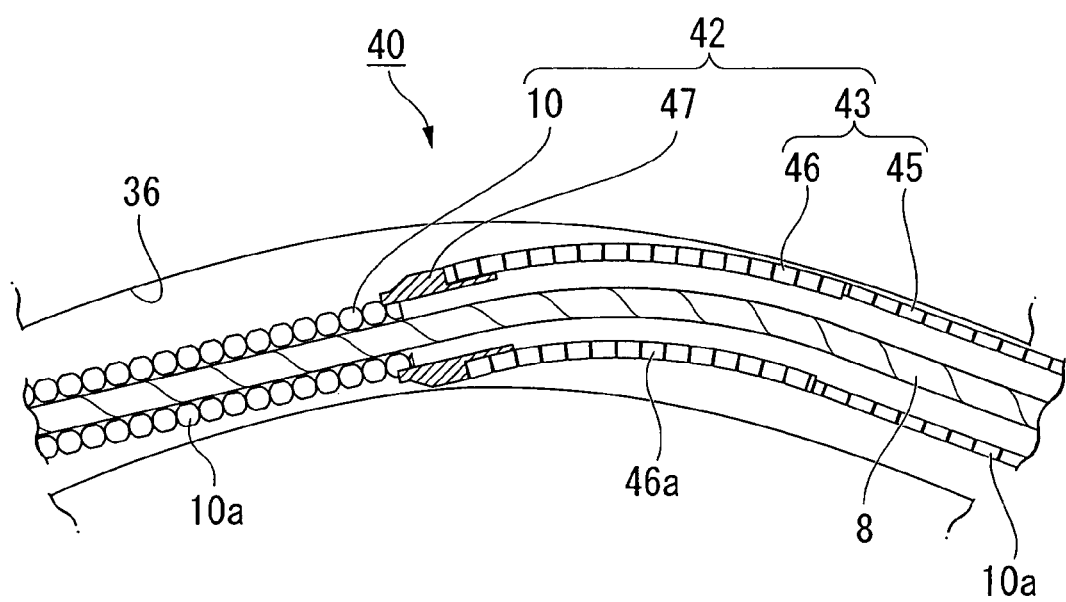
FIG. 12 is an explanatory diagram showing an action of the clip device in accordance with the second embodiment of the present invention.

Next, a second embodiment shall be described with reference to FIG. 11 and FIG. 12.

Note that constituent elements similar to those in the first embodiment shall be given the same reference numerals and explanations thereof shall be omitted here.

The point of difference between the second embodiment and the first embodiment is that a distal end side coil 43 in a tubular body 42 of an insertion portion 41 of a clip device 40 in accordance with the second embodiment is additionally provided with a first distal end side coil (coil) 45 which locates further to the distal end side and a second distal end side coil (second coil, coil) 46 on the proximal end side.

The second distal end side coil 46 and the proximal side coil 10 are connected to a coil connecting pipe 47 respectively.

The first distal end side coil 45 is wound by the flat wire 11a of the distal end side coil 11 in accordance with the first embodiment, and has a constant outer diameter and an inner diameter that are identical to the distal end side coil 11. The axial direction length of the first distal end side coil 45 is longer than the hook not shown that is disposed on the operation wire 8 and the moving distance of the clip unit.

The distal end of the second distal end side coil 46 is fixed to the proximal end of the first distal end side coil 45 by welding or the like. The length of the side of the flat wire 46a of the second distal end side coil 46 that is vertical to the coil center axial line C is longer than the flat wire 11a of the first distal end side coil 45. That is, by the winding of the flat wire 46a, the outer diameter is approximately the same as the first distal end side coil 45, while the inner diameter thereof is less than the first distal end side coil 45 and greater than the proximal side coil (coil) 10.

Therefore, a step portion 43a is formed at the boundary portion between the first distal end side coil 45 and the second distal end side coil 46, the size of which is such that the hook and clip unit not shown disposed on the operation wire 8 cannot be inserted therethrough. It is therefore arranged such that the inner diameters of each coil 45, 46, 10 becomes progressively smaller from the first distal end side coil 45 on the distal end side toward the proximal side coil 10 on the proximal end side.

The outer surface side of the proximal end portion of the second distal end side coil 46 is ground to a predetermined depth. The second distal end side coil 46 and the proximal side coil 10 are connected via the coil connecting pipe 12.

Here, letting the spring constant per unit length of the first distal end side coil 45 be k1, the spring constant per unit length of the proximal side coil 10 be k2, and the spring constant per unit length of the second distal end side coil 46 be k3, the magnitudes of the three spring constants per unit length are in the relation of k1<k3<k2. Here, the ratio of the spring constants per unit length of the second distal end side coil 46 and the first distal end side coil 45 is greater than 1.0 and less than or equal to 2.0.

Here, in the case of the proximal side coil 10 being wound with round wire, letting the longitudinal elastic modulus be E, the torsion spring constant per unit length kt1 of the proximal side coil 10 is expressed as Equation (3).

$$Kt1 = \frac{Ed^4}{64Dn} \quad (3)$$

Also, the torsion spring constant per unit length kt2 of the second distal end side coil 46 is expressed as Equation (4).

$$Kt2 = \frac{Eba^3}{12\pi Dn} \quad (4)$$

The proximal side coil 10 in the present embodiment is wound with flat wire 10a that is formed of flattened round wire. Accordingly, the torsion spring constant per unit length is calculated with Equation (4). Here, similarly to the first embodiment, the ratio of the spring constants per unit length of the proximal side coil 10 and the second distal end side coil 46 may be a value greater than 2.0. However, in this case, the torsion spring constant per unit length kt2 of the second distal end side coil 46 which has a smaller spring constant per unit length should be 25 Nmm/rad or more.

Next, the action of the clip device 40 in accordance with to the present embodiment shall be described.

Similarly to the first embodiment, the insertion portion 2 of the clip device 40 on which the clip unit is mounted is inserted through the treatment instrument insertion channel 36 that is curved, and the operation portion 5 is operated to indwell the clip in biological tissue.

At this time, a compressive force is loaded on the insertion portion 2 of the clip device 40 until the thin diameter portion 30A of the coupling member 30 breaks following the closure of the pair of arms 27b and 27c of the clip 27, similarly to the first embodiment. For this reason, in the vicinity of the distal end side connecting portion 47A of the coil connecting pipe 47 at which the hardness discontinuously changes, a bending stress occurs on the side of the second distal end side coil 46 which has a smaller spring constant per unit length.

However, in accordance with the clip device 40, even if the ratio of the spring constants per unit length of the proximal side coil 10 and the second distal end side coil 46 is greater than 2.0, the torsion spring constant per unit length kt2 of the second distal end side coil 46 which has a smaller spring constant per unit length is not less than 25 N mm/rad. Accordingly, even if a compressive force is loaded in the axial direction in the state of the tubular body 42 being curved, it is possible to suppress concentration of bending stress at the proximal end portion of the second distal end side coil 46 which has a smaller spring constant per unit length.

Figure 13:
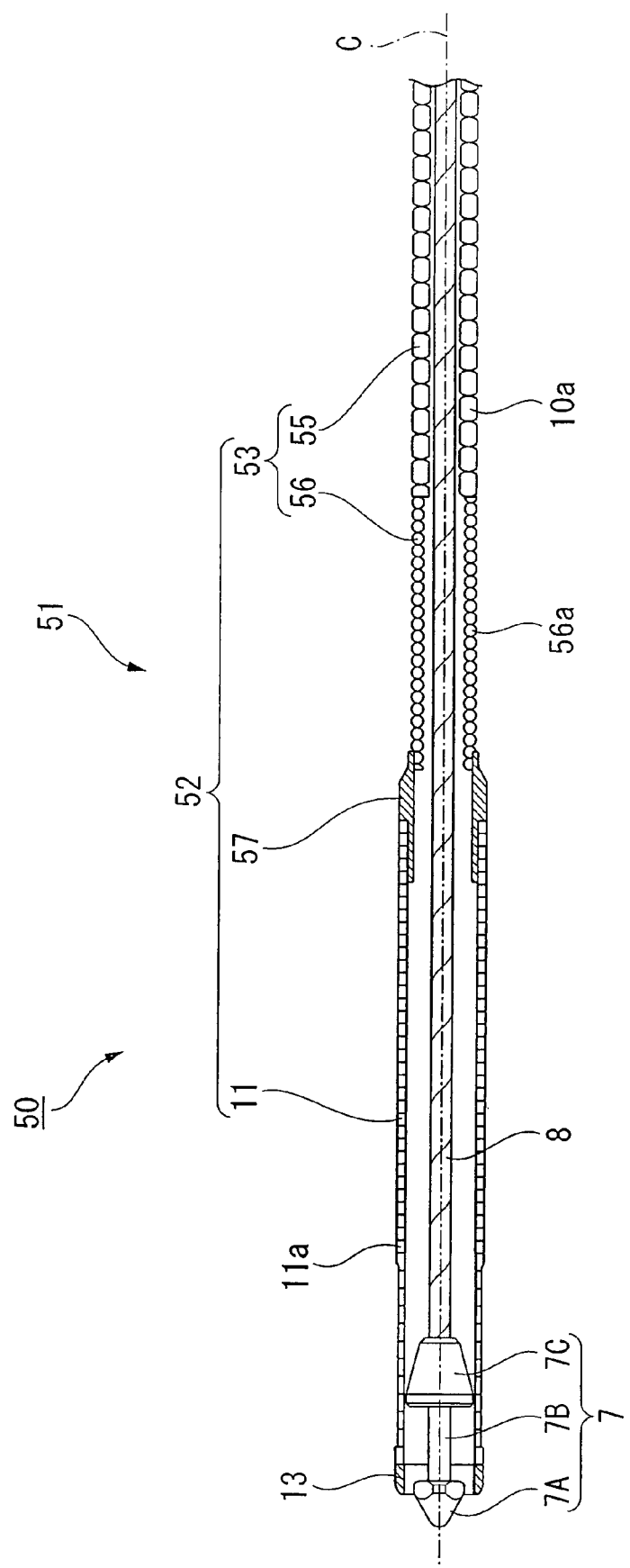
FIG. 13 is a sectional view showing a substantial part of the clip device in accordance with the third embodiment of the present invention.
Figure 14:
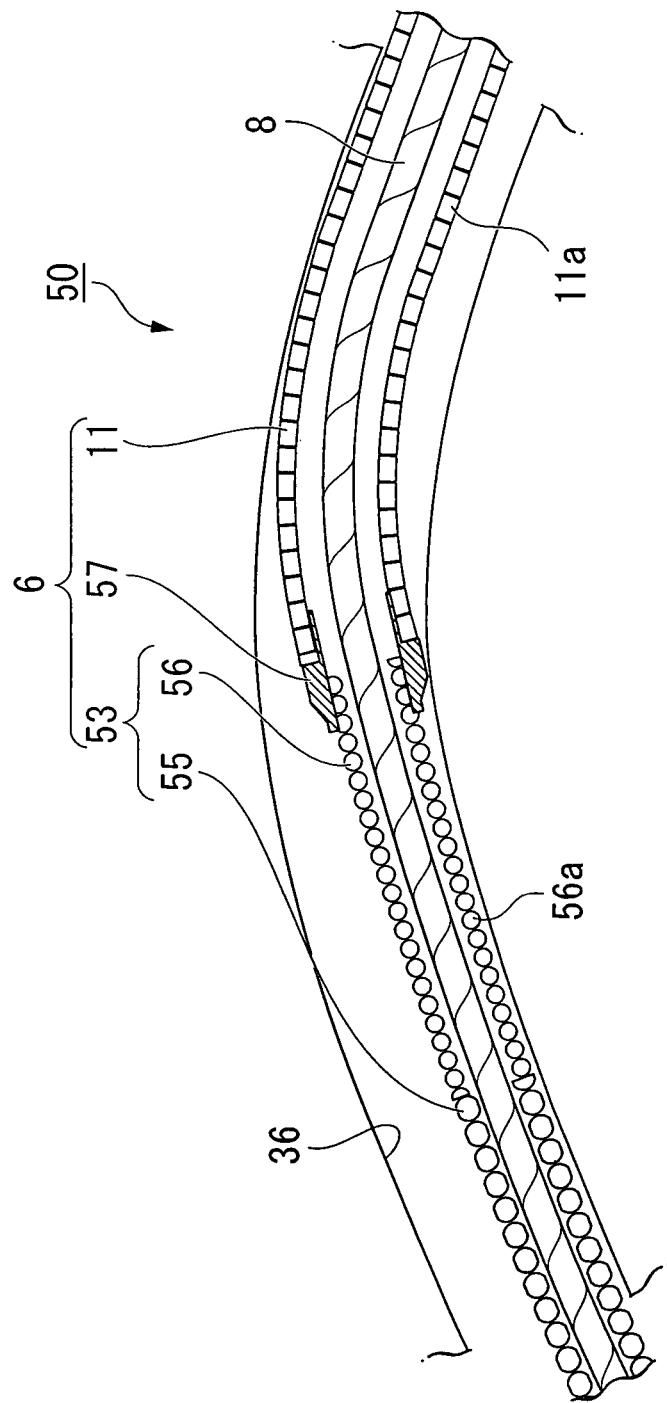
FIG. 14 is an explanatory diagram showing an action of the clip device in accordance with the third embodiment of the present invention.

Next, a third embodiment shall be described with reference to FIG. 13 and FIG. 14.

Note that constituent elements similar to those in the embodiments described above shall be given the same reference numerals and explanations thereof shall be omitted here.

The point of difference between the third embodiment and the first embodiment is that a proximal side coil 53 in a tubular body 52 of an insertion portion 51 of a clip device 50 in accordance with the present embodiment is provided with a first proximal side coil 55 having a constitution substantially the same as the proximal side coil 10 in accordance with the first embodiment and a second proximal side coil 56 (first coil) that is connected to the distal end of the first proximal side coil 55.

The second proximal side coil 56 is constituted by being wound with round wire 56a that is finer than the flat wire 10a of the first proximal side coil 55. The outer diameter of the first proximal side coil 55 is approximately the same as the outer diameter of the second proximal side coil 56, while the inner diameter of the first proximal side coil 55 is smaller than the inner diameter of the second proximal side coil 56. The proximal end of the distal end side coil 11 and the distal end of the second proximal side coil 56 are connected via a coil connecting pipe 57.

Letting the spring constant per unit length of the first proximal side coil 55 be k1, the spring constant per unit length of the distal end side coil 11 be k2, and the spring constant per unit length of the second proximal side coil 56 be k3, the magnitudes of the three spring constants per unit length are in the relation of k1>k2>k3. Here, the ratio of k1 and k3 may be greater than 2.0. The ratio of k2 and k3 is greater than 1.0 and less than or equal to 2.0.

The clip device 50 can exhibit the same action and effect as the clip device 40 in accordance with the second embodiment.

The technical scope of the present invention is not limited to the aforementioned embodiments, and it is possible to add various alterations without departing from the spirit or scope of the present invention.

For example, in the first embodiment, the ratio of the spring constants per unit length of the proximal side coil 10 and the distal end side coil 11 is greater than 1.0 and less than or equal to 2.0. However, the ratio of the spring constants per unit length maybe greater than 2.0, if the torsion spring constant per unit length of the distal end side coil is 25 N mm/rad or more.

In accordance with the first aspect of the present invention, since the ratio of the spring constants per unit length of the first coil and the second coil is greater than 1.0 and less than or equal to 2.0, even if a compressive force is loaded in the axial direction in the state of the tubular body being curved, it is possible to suppress concentration of bending stress at the end portion of the coil which is a side with a smaller spring constant.

In accordance with the second aspect of the present invention, since, among the first coil or the second coil, the torsion spring constant per unit length of the coil with the smaller spring constant per unit length is not less than 25 N mm/rad, even if a compressive force is loaded in the state of the tubular body being curved, twisting of the coil with the smaller spring constant per unit length is suppressed. Also, since the torsion spring constant is large, in addition to suppressing stress concentration, it is possible to hinder slippage even during stress concentration.

In accordance with the fifth aspect of the present invention, since the distal end side of the tubular body is soft, when inserted in the curved treatment instrument insertion channel, it readily curves along the treatment instrument insertion channel, and so can improve operability.

In accordance with the sixth aspect of the present invention, even if the hard connecting portion is provided, it is possible to ensure that stress concentration does not occur at the coil end in the vicinity of the connecting portion.

In accordance with the present invention, even if a strong compressive force is impressed on a tubular body in a curved treatment instrument channel, it is possible to suppress the plastic deformation of the tubular body due to the slippage of the coil wires.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A treatment instrument for an endoscope, the treatment instrument comprising:
   a coil-shaped tubular body that is configured to be inserted through a curvable treatment instrument insertion channel of the endoscope, the coil-shaped tubular body comprising:
      a first coil that has a spring constant per unit length of 15 N/mm to 500 N/mm; and
      a second coil that has a spring constant per unit length of 15 N/mm to 500 N/mm,
      wherein the spring constant per unit length of the second coil differs from the spring constant per unit length of the first coil,
      wherein the second coil is coaxially connected with the first coil, and
      wherein the ratio of the spring constant per unit length of the first coil and the spring constant per unit length of the second coil is greater than 1.0 and less than or equal to 2.0.

2. A treatment instrument for en endoscope, the treatment instrument comprising:

a coil-shaped tubular body that is configured to be inserted through a curvable treatment instrument insertion channel of the endoscope, the coil-shaped tubular body comprising:
 a first coil that has a spring constant per unit length of 15 N/mm to 500 N/mm; and
 a second coil that has a spring constant per unit length of 15 N/mm to 500 N/mm,
 wherein the spring constant per unit length of the second coil differs from the spring constant per unit length of the first coil,
 wherein the second coil is coaxially connected with the first coil, and
 wherein the torsion spring constant per unit length of either the first coil or the second coil with a smaller spring constant per unit length is not less than 25 N mm/rad.

3. The treatment instrument for an endoscope in accordance with claim 1 or claim 2, wherein
 the first coil is disposed at the proximal end side of the tubular body, and
 the second coil is connected to the distal end of the first coil.

4. The treatment instrument for an endoscope in accordance with claim 1 or claim 2, wherein the inner diameter of the second coil is greater than the inner diameter of the first coil.

5. The treatment instrument for an endoscope in accordance with claim 3, wherein the inner diameter of the second coil is greater than the inner diameter of the first coil.

6. The treatment instrument for an endoscope in accordance with claim 1 or claim 2, wherein
 the first coil is disposed at the proximal end side of the tubular body,
 the second coil is connected to the distal end of the first coil,
 the inner diameter of the second coil is formed to be greater than the inner diameter of the first coil, and
 the spring constant per unit length of the first coil is greater than the spring constant per unit length of the second coil.

7. The treatment instrument for an endoscope in accordance with claim 1 or claim 2, further comprising a connecting portion that has a greater hardness than the first coil and the second coil and that connects the first coil and the second coil.

8. The treatment instrument for an endo scope in accordance with claim 3, further comprising a connecting portion that has a greater hardness than the first coil and the second coil and that connects the first coil and the second coil.

9. The treatment instrument for an endo scope in accordance with claim 4, further comprising a connecting portion that has a greater hardness than the first coil and the second coil and that connects the first coil and the second coil.

10. The treatment instrument for an endoscope in accordance with claim 5, further comprising a connecting portion that has a greater hardness than the first coil and the second coil and that connects the first coil and the second coil.

11. The treatment instrument for an endoscope in accordance with claim 6, further comprising a connecting portion that has a greater hardness than the first coil and the second coil and that connects the first coil and the second coil.

\* \* \* \* \*